(12) United States Patent
Monti-Bloch

(10) Patent No.: US 8,309,539 B2
(45) Date of Patent: Nov. 13, 2012

(54) ACUTE TREATMENT OF SOCIAL PHOBIA

(75) Inventor: Louis Monti-Bloch, Mountain View, CA (US)

(73) Assignee: Pherin Pharmaceuticals, Inc., Los Altos, CA (US)

(*) Notice: Subject to any disclaimer, the term of this patent is extended or adjusted under 35 U.S.C. 154(b) by 931 days.

(21) Appl. No.: 11/223,882

(22) Filed: Sep. 9, 2005

(65) Prior Publication Data

US 2007/0059249 A1 Mar. 15, 2007

(51) Int. Cl.
*A61L 9/04* (2006.01)
*A61K 31/57* (2006.01)

(52) U.S. Cl. .......................... 514/178; 424/45
(58) Field of Classification Search .................. 514/178; 424/45
See application file for complete search history.

(56) References Cited

U.S. PATENT DOCUMENTS

| 5,883,087 A | 3/1999 | Berliner |
| 5,965,552 A * | 10/1999 | Berliner et al. ............... 514/182 |
| 6,066,627 A * | 5/2000 | Jennings-White et al. ... 514/177 |
| 6,117,860 A | 9/2000 | Jennings-White et al. |
| 6,225,057 B1 | 5/2001 | Estivill Palleja et al. |

FOREIGN PATENT DOCUMENTS

| WO | 96/10031 A1 | 4/1996 |
| WO | 98/03207 A1 | 1/1998 |

OTHER PUBLICATIONS

Ballenger (Current Treatments of the Anxiety Disorder in Adults, Society of Biological Psychiatry, 1999, p. 1579-1594).*

Blanco C. et al., "Pharmacotherapy of Social Anxiety Disorder", Society of Biological Psychiatry, vol. 51, No. 1, pp. 109-120, (2002).
A.I. Graul, "Compendium of Drugs for Psychiatric Disorders and Substance Abuse", Drugs of the Future, Prous Science, Spain, v. 28(11), pp. 1103-1144, Jan. 1, 2003 (date per EPO Supplementary Search Report).
N.E. Mealy et al. "PH-80/PH-94B", Drugs of the Future, Prous Science, Spain, v. 29(9), p. 963, Sep. 1, 2004 (date per EPO Supplementary Search Report).
Beers, MH and Berkow, R, eds., "The Merck Manual of Diagnosis and Therapy", 17th edition, 1999, Section 187—Anxiety Disorders, pp. 1512-1519, Merck Research Laboratories, Whitehouse Station, New Jersey.

* cited by examiner

*Primary Examiner* — San-Ming Hui
*Assistant Examiner* — Kathrien Cruz
(74) *Attorney, Agent, or Firm* — Hamilton DeSanctis & Cha, LLP

(57) ABSTRACT

Methods and compositions for the treatment of social phobia are provided, including administering a therapeutically effective amount of an androsta-4,16-dien-3-ol steroid to an individual in need of treatment and a pharmaceutical composition for the treatment of social phobia having a therapeutically effective amount of an androsta-4,16-dien-3-ol steroid. Therapeutically effective amounts may be, for example, between about 100 picograms and about 100 micrograms, or between about 1 nanogram and about 10 microgram, or between about 10 nanograms and about 1 microgram of an androsta-4,16-dien-3-ol steroid. Administration of the androsta-4,16-dien-3-ol compound is preferably intranasal administration to the nasal passages and the vomeronasal organ of the individual. A preferred androsta-4,16-dien-3-ol steroid is [3β]-androsta-4,16-dien-3-ol. In some embodiments of the methods, both [3β]-androsta-4,16-dien-3-ol and [3α]-androsta-4,16-dien-3-ol are administered to a patient, and are included in a pharmaceutical composition for the treatment of social phobia.

22 Claims, No Drawings

ACUTE TREATMENT OF SOCIAL PHOBIA

FIELD OF THE INVENTION

This invention relates to method and compositions for treating social phobia.

BACKGROUND TO THE INVENTION

U.S. Pat. No. 5,883,087, "Androstane steroids as neurochemical initiators of change in human hypothalamic function and related pharmaceutical compositions and methods", discloses a number of androstanes as vomeropherins, i.e. compounds that act on the vomeronasal organ of a human to alter hypothalamic function, and claims a method of altering a hypothalamic function of an individual by administering to the vomeronasal organ of the individual a unit dose of up to about 100 µg of androsta-4,16-dien-3β-ol, such as administering to a woman to result in reduction of premenstrual stress. U.S. Pat. No. 5,965,552, a continuation of U.S. Pat. No. 5,883,087, claims a method of reducing anxiety by vomeronasal administration of androsta-4,16-dien-3β-ol. However, neither of these patents identify "anxiety" in any detail or disclose any data demonstrating the claimed effect.

The *Diagnostic and Statistical Manual of Mental Disorders*—Fourth Edition, DSM-IV-TR (Text Revision), Washington D.C., USA, 2000, is the standard diagnostic manual for mental disorders. It divides anxiety disorders into several categories and sub-categories: acute stress disorder, agoraphobia, generalized anxiety disorder, obsessive-compulsive disorder, panic disorder (with or without agoraphobia), post-traumatic stress disorder, and phobias (including specific phobia and social phobia).

Social phobia, also called social anxiety disorder, is classified under DSM Code 300.23, and is characterized by:
(a) a marked and persistent fear of one or more social or performance situations in which the person is exposed to unfamiliar people or to possible scrutiny by others. The individual fears that he or she will act in a way (or show anxiety symptoms) that will be humiliating or embarrassing;
(b) exposure to the feared social situation almost invariably provokes anxiety, which may take the form of a situationally bound or situationally predisposed panic attack;
(c) the person recognizes that the fear is excessive or unreasonable;
(d) the feared social or performance situations are avoided or else are endured with intense anxiety or distress; and
(e) the avoidance, anxious anticipation, or distress in the feared social or performance situation(s) interferes significantly with the person's normal routine, occupational (academic) functioning, or social activities or relationships, or there is marked distress about having the phobia; and
(g) the fear or avoidance is not substance-induced or due to a general medical condition or another mental disorder.

The onset of social phobia often occurs early in life, although in many cases individuals begin to suffer from it in adolescence or adulthood. Social phobia is reported to be the most common anxiety disorder with a 1-year prevalence of 7% to 8% and a lifetime prevalence of 13% to 14%. It is diagnosed slightly more often in women than in men. Social phobia tends to be a chronic disorder with periods of exacerbation, with a reported mean duration of illness of approximately 20 years. It is believed that there may be a genetic component to social phobia, as close relatives of sufferers from social phobia are at higher risk than the general population. Given the high degree of burden of illness in social phobia, its treatment has become a major priority.

Current treatments for social phobia include both psychosocial and pharmacologic measures. Two important psychosocial treatments are exposure therapy and cognitive behavioral therapy, while pharmacological measures vary widely and are of two types: chronic treatments and acute treatments.

Chronic treatments for social phobia are treatments that are administered chronically, whether or not the sufferer from social phobia is about to experience or is experiencing a social or performance situation.

These treatments generally involve the administration of the drugs that are commonly used for generalized anxiety disorder or panic disorder, such as monoamine oxidase inhibitors (MAOs, e.g., phenelzine, tranylcypromine, seligiline and pergolide) and tricyclic antidepressants (e.g. nortriptyline and amitriptyline), and, more recently, selective serotonin reuptake inhibitors (SSRIs, e.g., fluoxetine and paroxetine) and serotonin-norepinephrine reuptake inhibitors (SNRIs, e.g. venlafaxine and nefazodone).

While these treatments are reasonably effective in preventing the anxiety/panic of social phobia when the sufferer experiences a social or performance situation, they have at least three significant drawbacks.

The first is that they have a very slow onset of action. Each of these drugs requires a period of several weeks before becoming efficacious, although once this initial period is passed, they remain effective with chronic administration. Thus these drugs cannot be used to provide rapid relief when a sufferer from social phobia encounters a social or performance situation.

The second is that their use is frequently accompanied by significant undesirable side effects. For example, MAOIs are associated with postural hypotension, sustained mild elevation of diastolic blood pressure, reactions to certain foodstuffs (e.g. cheese and red wine); tricyclics are associated with cardiac toxicity, orthostatic hypotension, dizziness, tachycardia, palpitations, blurred vision, dry mouth, urinary retention and prostate hypertrophy; and SSRIs and SNRIs are frequently associated with sexual dysfunction, headaches and nausea. Therefore, the efficacy from these drug therapies must be always be weighed carefully against the potential adverse effects of the drug.

The third is that that there is not available evidence through controlled clinical research showing that continuation drug therapy or maintenance drug therapy with the above mentioned pharmacological treatments is effective in preventing relapse or recurrences.

Also, these chronic treatments may well be also unsatisfactory to sufferers whose social phobia is not severe, either because they have a higher threshold for the onset of social phobia anxiety/panic in response to a social or performance situation or because their level of anxiety/panic when a social or performance situation is experienced is lower.

Acute treatments for social phobia are treatments that are administered when the sufferer is about to experience or is already experiencing a social or performance situation.

Beta-blockers such as seligiline and pergolide are used as an acute treatment for social phobia, but are only effective when dosed sufficiently in advance of the triggering event that the drug (which is administered orally) is absorbed from the GI tract, enters the circulatory system, crosses the blood-brain barrier, and binds to receptors in the brain. Thus, they must be administered at least 30 to 60 minutes before the sufferer experiences the triggering event. They are therefore of only limited value because a sufferer from social phobia may not be able to predict the occurrence of a triggering event and prepare for it by administering the beta-blocker; and their use is frequently accompanied by undesirable side effects such as postural hypotension, sustained mild elevation of diastolic blood pressure and reactions to certain foods.

There are no current acute treatments for social phobia that are effective in relieving social phobia anxiety once the sufferer is already experiencing a social or performance situation.

There is therefore a need for an effective treatment for social phobia, including a treatment that can be effectively administered when a sufferer from social phobia is about to experience or is even already experiencing a social or performance situation as acute treatment, especially a treatment that can be effectively administered when the sufferer is already experiencing a social or performance situation; and especially a treatment that is not accompanied by the undesirable side effects that are associated with current treatments.

SUMMARY OF THE INVENTION

Methods of treating social phobia in an individual include administering a therapeutically effective amount of an androsta-4,16-dien-3-ol steroid to the individual. In some embodiments of the methods, a therapeutically effective amount of an androsta-4,16-dien-3-ol steroid is administered to a patient, and in some embodiments of the compositions, a therapeutically effective amount of an androsta-4,16-dien-3-ol is included in a pharmaceutical composition for the treatment of social phobia. Therapeutically effective amounts may be, for example, between about 100 picograms and about 100 micrograms, or between about 1 nanogram and about 10 microgram, or between about 10 nanograms and about 1 microgram of an androsta-4,16-dien-3-ol. The androsta-4,16-dien-3-ol compound is preferably administered to the nasal passages and the vomeronasal organ of the individual. The individual is preferably a human subject. In embodiments, the androsta-4,16-dien-3-ol steroid is [3β]-androsta-4,16-dien-3-ol. In embodiments of the methods, the individual is a woman. In further embodiments, the androsta-4,16-dien-3-ol steroid is [3α]-androsta-4,16-dien-3-ol. In some embodiments of the methods, both [3β]-androsta-4,16-dien-3-ol and [3α]-androsta-4,16-dien-3-ol are administered to a patient, and in some embodiments of the compositions, both [3β]-androsta-4,16-dien-3-ol and [3α]-androsta-4,16-dien-3-ol are included in a pharmaceutical composition for the treatment of social phobia.

In one aspect, the present invention provides a method for the treatment of social phobia, comprising administering an effective amount of an androsta-4,16-dien-3-ol, such as androsta-4,16-dien-3β-ol, to the vomeronasal organ of a person in need of such treatment. In embodiments of the methods, the compound is preferably [3β]-androsta-4,16-dien-3-ol. In further embodiments, the methods may comprise the step of administering to the nasal passages and the vomeronasal organ of the individual both [3β]-androsta-4,16-dien-3-ol and [3α]-androsta-4,16-dien-3-ol. In embodiments, the step of administering may comprise administering to the nasal passages and the vomeronasal organ of the individual a unit dosage of an androsta-4,16-dien-3-ol. A unit dosage of androsta-4,16-dien-3-ol, such as a unit dosage of [3β]-androsta-4,16-dien-3-ol, may be up to about 100 micrograms of the compound or compounds. In embodiments of the invention, the amount of androsta-4,16-dien-3-ol, such as [3β]-androsta-4,16-dien-3-ol, that is administered to the patient is between about 100 picograms and about 100 micrograms. In other embodiments, the amount of the androsta-4,16-dien-3-ol compound or compounds, such as [3β]-androsta-4,16-dien-3-ol, that is administered is between about 1 nanogram and about 10 micrograms, or between about 10 nanograms and about 1 microgram.

Further aspects include the use of an androsta-4,16-dien-3-ol, such as androsta-4,16-dien-3β-ol, in the manufacture of a medicament for the treatment of social phobia; compositions for the treatment of social phobia, comprising an androsta-4,16-dien-3-ol, such as androsta-4,16-dien-3β-ol, and a nasally acceptable excipient; and devices for the treatment of social phobia, the devices containing an androsta-4,16-dien-3-ol, such as androsta-4,16-dien-3β-ol, and being adapted to deliver an effective dose of the androsta-4,16-dien-3-ol intranasally and to the vomeronasal organ. In embodiments, the devices for the treatment of social phobia contain androsta-4,16-dien-3β-ol and are adapted to deliver an effective dose of the androsta-4,16-dien-3β-ol intranasally and to the vomeronasal organ.

The methods may also include preparing a pharmaceutical composition of an androsta-4,16-dien-3-ol compound, such as [3β]-androsta-4,16-dien-3-ol, dissolved in a pharmaceutically acceptable carrier. The pharmaceutical composition may be an ointment, a powder, a liquid, or an aerosol. The methods also include preparing a pharmaceutical composition containing [3α]-androsta-4,16-dien-3-ol, or may include preparing a pharmaceutical composition containing both [3β]-androsta-4,16-dien-3-ol and [3α]-androsta-4,16-dien-3-ol, in which the androsta-4,16-dien-3-ol compound or compounds may be dissolved in a pharmaceutically acceptable carrier, an ointment, a powder, a liquid, or an aerosol.

The novel methods and compositions disclosed herein also include a pharmaceutical composition adapted for nasal administration in a human subject for alleviating the symptoms of social phobia. Such a pharmaceutical composition includes a therapeutically effective amount of an androsta-4,16-dien-3-ol steroid and a pharmaceutically acceptable carrier. The androsta-4,16-dien-3-ol steroid may be [3β]-androsta-4,16-dien-3-ol, [3α]-androsta-4,16-dien-3-ol, or both. These substances belong to a family of steroids called "vomeropherins" that modulate brain function through stimulations of nasal chemosensory receptors. Such a pharmaceutical composition may have about 100 micrograms of androsta-4,16-dien-3-ol steroid in a pharmaceutically acceptable carrier, or may have between about 100 picograms and about 100 micrograms. In embodiments, the pharmaceutical composition includes between about 1 nanogram and about 10 micrograms of androsta-4,16-dien-3-ol, or between about 10 nanograms and about 1 microgram of androsta-4,16-dien-3-ol. The pharmaceutically acceptable carrier may be combined with the androsta-4,16-dien-3-ol to provide an ointment, a powder, a liquid, or an aerosol. Thus, the pharmaceutical compositions may include [3β]-androsta-4,16-dien-3-ol, [3α]-androsta-4,16-dien-3-ol or both.

Preferred embodiments of the invention include one or more of the following:
(a) androsta-4,16-dien-3β-ol is the sole active ingredient administered;
(b) the androsta-4,16-dien-3β-ol is administered for the acute treatment of social phobia, or (b1) the androsta-4,16-dien-3β-ol is administered for the chronic treatment of social phobia,
(c) the androsta-4,16-dien-3β-ol is administered in a pharmaceutical composition and/or by a delivery device;
(d) the composition contains androsta-4,16-dien-3α-ol and an excipient. Since androsta-4,16-dien-3α-ol is odorless, the composition includes and odorant as excipient to ensure that the administration is reaching the nasal passages, this will also help to enhance the effect of androsta-4,16-dien-3α-ol.

e) an effective amount of the androsta-4,16-dien-3β-ol administered to the vomeronasal organ may be between about 100 μg and about 100 μg, especially between about 1 ng and about 10 μg, particularly between about 10 ng and about 1 μg. The ratio of the vomeronasal organ receptor area to the area covered by the delivery device plume is typically about 100:1. Therefore, the effective amount of androsta-4,16-dien-3α-ol administered intranasally is between about 10 μg and about 10 mg, especially between about 1 μg and about 1 mg, particularly between about 1 μg and about 100 μg. For administration of androsta-4,16-dien-3α-ol to the nostril, formulated in an ointment, the effective amount of androsta-4,16-dien-3α-ol in the ointment is between about 100 μg and about 100 mg, especially between about 100 μg and about 10 mg, particularly between about 10 μg and about 1 mg.

DETAILED DESCRIPTION OF THE INVENTION

When nasally administered to human subjects, androsta-4,16-dien-3-ol steroids, and particularly [3β]-androsta-4,16-dien-3-ol, are effective to treat social anxiety disorder in human individuals, particularly human females. These compounds are believed to specifically bind to chemosensory receptors of certain nasal neuroepithelial cells and it is believed that this binding generates a series of neurophysiological responses that aid in the alleviation of symptoms and in the treatment of social anxiety disorder in humans. One or both enantiomers of androsta-4,16-dien-3-ol steroids may be administered to a human subject to treat social anxiety disorder. The β enantiomer, [3β]-androsta-4,16-dien-3-ol (also termed "androsta-4,16-dien-3β-ol"), appears to be more potent and is odorless. The a enantiomer ([3α]-androsta-4,16-dien-3-ol (also termed "androsta-4,16-dien-3α-ol")) has a pleasant odor, and may be administered to patients and included in compositions with the β enantiomer to impart a pleasant odor as well as for its pharmacological effects.

The chemical structures of the two enantiomers of androsta-4,16-dien-3-ol are illustrated below, with [3β]-androsta-4,16-dien-3-ol shown as Formula I:

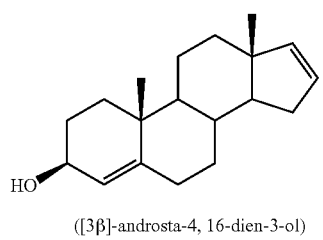

Formula I ([3β]-androsta-4, 16-dien-3-ol)

And [3α]-androsta-4,16-dien-3-ol shown as Formula II:

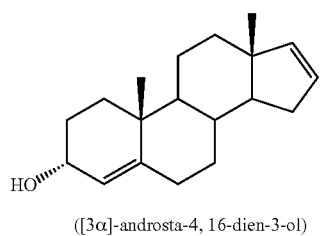

Formula II ([3α]-androsta-4, 16-dien-3-ol)

Definitions

"Social phobia" (also termed "social anxiety disorder") is a mental disorder having the diagnostic characteristics discussed above, and as defined under DSM Code 300.23 as discussed in the BACKGROUND TO THE INVENTION.

A "social or performance situation" in social phobia includes a situation in which a person is in a place or situation from which escape may not be immediately available; persistent fear that one or more situations may expose a person to unusual or unacceptable scrutiny by others causing the person to act inappropriately; and persistent fear of a circumscribed object or situation. Exposure to these stimuli will usually lead to immediate symptoms of anxiety. Thus, examples include being told of the imminent occurrence of a social situation in which the sufferer fears embarrassment (such as being told that one must give a speech), and the actual occurrence of a social situation in which the sufferer fears embarrassment (such as being introduced to a group of strangers). Anticipatory anxiety is common, and sufferers of social phobia typically attempt to avoid these stimuli, which can lead to disruption in daily living.

"Response" is the response experienced by the sufferer during the crisis situation (e.g., symptoms of anxiety including panic attack, tachycardia, sweating and breathing difficulty).

"Acute treatment" of social phobia includes reducing the level of response in a person suffering from social phobia who is experiencing a triggering event and reducing or preventing the social phobia response in a person suffering from social phobia who is about to experience a social or performance situation (including, in both cases, both raising the threshold for the onset of the response and decreasing the intensity of the response). An acute treatment is intended to have a relatively temporary effect of relatively short duration, such as less than about one hour or less than about five hours in duration.

"Chronic treatment" of social phobia includes reducing the level of response in a person suffering from social phobia on a relatively long-term basis, or on a continuing basis. Such a treatment may have effects including, for example, both raising the threshold for the onset of the response and decreasing the intensity of the response. A chronic treatment is intended to have a relatively extended effect of relatively long duration, such as more than about five hours, or more than about one day, or more than about two days in duration.

"Continuation treatment" of social phobia includes daily administration of androsta-4,16-dien-3β-ol, to include both treatment with a relatively short period of action (e.g. a few hours) and treatment of relatively longer duration (e.g. over a period of many days, and including repeated administrations over one, two, or more days). Treatment for a short period may be particularly suited for, e.g., treatment for the business day or for an evening social event. Treatment for a relatively longer duration may be particularly suited for situations expected to last for a longer period of time. In either case, such treatments are directed at reducing the level of response in a person suffering from social phobia who is experiencing a social or performance situation and reducing or preventing the social phobia response in a person suffering from social phobia who is about to experience a social or performance situation (including, in both cases, raising the threshold for the onset of the response and decreasing the intensity of the response).

An "effective amount" of androsta-4,16-dien-3β-ol is the amount that, when administered to the vomeronasal organ of a person suffering from social phobia, is sufficient to achieve treatment of the social phobia. The effective amount is an amount that, if administered systemically, would be ineffective to achieve treatment of the social phobia but that is effective when administered to the VNO.

"Comprising" is a term of inclusion and not of limitation, and requires the presence of the named element while not excluding the presence of other elements. Thus, for example, a composition comprising androsta-4,16-dien-3β-ol is one containing androsta-4,16-dien-3β-ol and optionally containing other active ingredients and/or excipients.

Unless the context requires otherwise, the singular includes the plural. Thus, for example, "an excipient" may include one or more excipients.

A "chronic" treatment is a treatment intended to have a therapeutic effect of relatively long duration. For example, a chronic treatment may be intended to have a therapeutic effect with a duration of greater than about five hours; or greater than about one day; or greater than about two days; or more.

An "acute" treatment is a treatment intended to have a therapeutic effect of relatively short duration. For example, an acute treatment may be intended to have a therapeutic effect of less than about five hours; or of less than about three hours; or of less than about one hour; or less.

Vomeronasal Organ and Vomeropherins

The vomeronasal organ ("VNO"; also known as "Jacobson's organ") is a bilateral chemosensory organ found in most vertebrates including humans. In mammals, this organ is accessed through the nostrils, and has been associated with pheromone reception in most species (see generally Muller-Schwarze and Silverstein, Chemical Signals, Plenum Press, New York (1980); Monti-Bloch, L., et al., Journal of Steroid Biochemistry and Molecular Biology (1991). Vol. 39 (4): 573-582; Monti-Bloch, L., et al., Annals of the New York Academy of Sciences (1998). Vol. 855: 373-389). The axons of the neuroepithelia of the vomeronasal organ, located supra palatinal, form the vomeronasal nerve and have direct input to the hypothalamus and limbic amygdala of the brain. The distal axons of the terminals nerve neurons may also serve as chemosensory receptors in the VNO (Stensaas, L. J. et al., Journal of Steroid Biochemistry and Molecular Biology (1991). Vol. 39 (4): 553-560). This nerve has direct synaptic connection with the hypothalamus.

Human pheromones delivered to the vomeronasal organ area bind to local receptors and trigger nerve signals that reach the brain inducing physiological and behavioral changes (Grosser, B. I. et al., Psychoneuroendocrinology (2000) Vol. 25: 289-299). A new family of synthetic analogs of human pheromones, called vomeropherins (defined as substances that bind to receptors in the VNO), can induce robust physiological, pharmacological and behavioral changes when delivered airborne to the VNO. This information is supported by several studies in human volunteers using functional magnetic resonance imaging (fMRI) and positron emission tomography (P.E.T.), showing that vomeropherins selectively activate the brain areas (hypothalamus, limbic system, cingulate gyrus, anterior thalamus and prefrontal cortex) where their physiological, pharmacological and behavioral effects are integrated.

Androsta-4,16-Dien-3β-ol

Androsta-4,16-dien-3β-ol is a vomeropherin commercially available from suppliers such as Steraloids, Inc., Newport, R.I., USA. It may be synthesized from the widely commercially available testosterone (17β-hydroxyandrost-4-en-3-one) by conversion to androsta-4,16-dien-3-one (also commercially available), followed by reduction to give a mixture of androsta-4,16-dien-3β-ol and its 3α-epimer, androsta-4,16-dien-3α-ol, and separation of the epimers by chromatography. This synthesis is disclosed in U.S. Pat. No. 5,883,087 and is summarized below.

Testosterone is treated with methyl chloroformate in pyridine to give 17β-methoxycarbonyloxyandrost4-en-3-one in 76% yield after recrystallization from methanol. A solution of the 17β-methoxycarbonyloxyandrost4-en-3-one in toluene is pyrolyzed at 460° C., and the crude product is recrystallized from acetone at room temperature to give androsta-4,16-dien-3-one in 90% yield. The androsta-4,16-dien-3-one is reduced at −55° with lithium tris(1,2-dimethylpropyl)hydridoborate in tetrahydrofuran to give a mixture of androsta-4,16-dien-3β-ol and androsta-4,16-dien-3α-ol; and chromatography on silica gel using dichloromethane/ethyl acetate gives pure androsta-4,16-dien-3β-ol and pure androsta-4,16-dien-3α-ol, each in 48% yield. These may be recrystallized (androsta-4,16-dien-3β-ol from cyclohexane at room temperature and androsta-4,16-dien-3α-ol from petroleum ether at −30° C.).

Social Phobia

The essential features (diagnostic criteria) of social phobia are defined in the DSM-IV-TR, in Section 300.23. Social phobia is the third most common psychiatric disorder after major depression and alcohol dependence. An essential criterion for the diagnosis of social phobia is a marked and persistent fear of most (typically several, and generally accepted as four or more) social or performance situations in which an individual believes embarrassment could occur as a consequence of exposure to unfamiliar people and/or possible scrutiny by others.

As discussed in the BACKGROUND TO THE INVENTION section above, Social phobia, also called social anxiety disorder (DSM Code 300.23) is characterized by:

(a) a marked and persistent fear of one or more social or performance situations in which the person is exposed to unfamiliar people or to possible scrutiny by others. The individual fears that he or she will act in a way (or show anxiety symptoms) that will be humiliating or embarrassing;

(b) exposure to the feared social situation almost invariably provokes anxiety, which may take the form of a situationally bound or situationally predisposed panic attack;

(c) the person recognizes that the fear is excessive or unreasonable;

(d) the feared social or performance situations are avoided or else are endured with intense anxiety or distress; and (e) the avoidance, anxious anticipation, or distress in the feared social or performance situation(s) interferes significantly with the person's normal routine, occupational (academic) functioning, or social activities or relationships, or there is marked distress about having the phobia; and (g) the fear or avoidance is not substance-induced or due to a general medical condition or another mental disorder.

There are two subtypes of social phobia: (i) generalized (discrete) social phobia, which affects about 75% of social phobia sufferers and in which fear and avoidance extend to a wide range of social situations, and (ii) specific (nongeneralized) social phobia, in which the social phobia sufferer fears only one or a few circumscribed situations. Speaking in front of an audience is by far the most prevalent of social fears associated with social phobia.

Social phobia has a lifetime comorbidity rate of approximately 81% with other psychiatric disorders (particularly affective disorders, other anxiety disorders, and substance abuse disorders), as well as to being associated with increased nonpsychiatric medical difficulties. Suicide attempts are more common among social phobia sufferers, and social phobia sufferers generally rate their illness as more intrusive, than do patients with a number of serious medical conditions (such as end-stage renal disease or laryngeal cancer). However, there is a strong consensus that social phobia is one of the least commonly recognized and treated mental disorders.

The Distinction Between Social Phobia and Generalized Anxiety Disorder

Generalized anxiety disorder (GAD) is classified under DSM code 300.02, and is characterized by:

(a) excessive anxiety and worry (apprehensive expectation), occurring more days than not for at least 6 months, about a number of events or activities;
(b) difficulty controlling the anxiety and worry;
(c) the anxiety and worry are associated with three or more of the following six symptoms, with at least some symptoms present for more days than not for the past 6 months: restlessness or feeling keyed up or on edge, being easily fatigued, difficulty concentrating or mind going blank, irritability, muscle tension, and sleep disturbance (difficulty falling or staying asleep, or restless unsatisfying sleep);
(d) the focus of the anxiety and worry is not confined to features of an Axis I disorder, e.g., the anxiety or worry is not about having a panic attack (as in panic disorder), being embarrassed in public (as in social phobia), being contaminated (as in obsessive-compulsive disorder), being away from home or close relatives (as in separation anxiety disorder), gaining weight (as in anorexia nervosa), having multiple physical complaints (as in somatization disorder), or having a serious illness (as in hypochondriasis), and the anxiety and worry do not occur exclusively during posttraumatic stress disorder;
(e) the anxiety, worry, or physical symptoms cause clinically significant distress or impairment in social, occupational, or other important areas of functioning; and
(f) the disturbance is not due to the direct physiological effects of a substance or a general medical condition and does not occur exclusively during a mood disorder, a psychotic disorder, or a pervasive mental disorder.

As indicated above, social phobia is characterized by a marked and persistent fear of one or more social situations; however, GAD does not share this characteristic feature. In addition, exposure to the feared situation almost always provokes anxiety; however, this is not a defining characteristic of GAD. In social phobia, the anxiety is tied closely to the event, and often is relieved upon removal from or cessation of the embarrassing situation or event (only to return upon subsequent anticipation or presentation of another occurrence of the embarrassing situation or event). However, this is not the case with GAD, which is not tied to a particular event and is typically not relieved by avoidance or cessation of a particular event.

Social phobia and general anxiety disorder are thus distinguishable. Since social phobia is related to the individual's fear of embarrassment or humiliation in public, and is typically tied to situations in which the individual fears they may be exposed to such public embarrassment or humiliation by the need to appear or perform in that situation, the individual attempts to avoid the anxiety-causing situations. This is not the case with generalized anxiety, which is not tied to particular social situations and which typically presents as a near-continual anxiety not related to any particular event or situation.

Sufferers from social phobia (particularly adult sufferers) will be aware that speaking in public, or taking a test, or preparing and serving a meal for a group of people, causes them anxiety. They will therefore avoid the situation if possible, or dread it if it is unavoidable. This differs from the response of sufferers from generalized anxiety, for whom a social situation which may expose them to public embarrassment or humiliation is not seen as particularly more anxiety-producing than other situations. As mentioned above, the anxiety caused by social phobia typically soon fades with cessation or distance from the triggering event, and reappears with the re-occurrence of the stressful event.

The anxiety of sufferers from generalized anxiety, on the other hand, may persist for long periods of time and is typically unrelated to particular situations or events; and sufferers may have felt anxious all their lives. Despite such constant anxiety, they may not realize that their worry is excessive, although they have trouble controlling their fears, or find that their worry interferes with their ability to function in social or occupational situations.

The following table shows a comparison of symptoms and behaviors in social phobia and generalized anxiety disorder.

| Symptom/anxiety-provoking event | Social phobia | GAD |
| --- | --- | --- |
| General anxiety | No | Yes |
| Fear of public embarrassment or humiliation | Yes | No |
| Anxiety in anticipation of particular social situations | Yes | No |
| Anxiety during particular social situations | Yes | No |
| Avoids particular social situation due to anxiety | Yes | No |
| Avoidance significantly interferes with normal life | Yes | No |
| Realizes fear is excessive or unreasonable | Yes | Not applicable |
| Hypersensitivity to criticism or rejection | Yes | No |
| Difficulty being assertive | Yes | No |
| Difficulty controlling the anxiety | Yes | Yes |
| Focus of anxiety is NOT social situation | No | Yes |

It is evident from the table that the symptoms or anxiety-provoking events for social phobia differ from those for GAD. Thus, although sufferers from social phobia experience anxiety, and may experience some of the same physical symptoms related to anxiety as do sufferers from GAD, the triggering events, symptoms and behavior of sufferers from social phobia are distinct from GAD. It would thus be expected that the effects of pharmacologic interventions would differ between the two disorders.

Pharmacological treatments directed at GAD are not specific for social phobia. Serotonin reuptake inhibitors have been developed for, and are prescribed to treat, depression. Monoamine oxidase inhibitors, norepinephrine reuptake inhibitors, tricyclic antidepressants, beta-blockers, and modulators of GABA-ergic neurotransmission are likewise not specific for anxiety, nor have they been found to be specifically useful in the treatment of social phobia. Although often of some efficacy, in many cases such treatments or poorly effective or even ineffective when given to persons suffering from social phobia.

Methods and Compositions for Treating Social Phobia

Disclosed herein are methods for the treatment of social phobia, comprising administering a therapeutically effective amount of an androsta-4,16-dien-3-ol steroid to the individual. In some embodiments, a therapeutically effective amount of an androsta-4,16-dien-3-ol steroid is administered to a patient, and in some embodiments of the compositions, a therapeutically effective amount of an androsta-4,16-dien-3-ol is included in a pharmaceutical composition for the treatment of social phobia. In some embodiments of the methods, the treatment of social phobia comprises administering an effective amount of an androsta-4,16-dien-3-ol steroid intranasally and to the vomeronasal organ. In some embodiments, the androsta-4,16-dien-3-ol steroid administered intranasally and to the vomeronasal organ is androsta-4,16-dien-3β-ol.

In an embodiment of the methods and compositions, [3β]-androsta-4,16-dien-3-ol, [3α]-androsta-4,16-dien-3-ol, or both, is administered nasally to a patient, providing nonsystemic delivery of the compounds effective to treat social phobia in the patient. In preferred embodiments, the compound is [3β]-androsta-4,16-dien-3-ol. Preferably, the patient is female.

The effective amount of androsta-4,16-dien-3β-ol administered was determined in dose-response studies where the amplitude of the mass receptor potential of the vomeronasal receptors (electrogram of the vomeronasal organ or electrovomerogram) was recorded from volunteers diagnosed with generalized anxiety disorder (GAD), while locally delivering different concentrations of the steroid in aerosol form, using a Multifunctional Miniprobe® described in U.S. Pat. No. 5,303,703. This electrovomerogram allows precise measuring of the concentration dependent effect of locally delivered androsta-4,16-dien-3β-ol to vomeronasal receptors, and calculation of the half-maximal concentration, the Effective Concentration 50 ($EC_{50}$).

Androsta-4,16-dien-3β-ol was delivered directly to the vomeronasal organ pit of anxious patients using the Multifunctional Miniprobe®, consisting of a concentric arrangement of Teflon® tubes having an inner non-polarized silver wire recording-electrode. For recording the effects of the steroid on the electrovomerogram, the recording end of the Multifunctional Miniprobe® was positioned in the surface mucosal membrane of the vomeronasal organ pit with the aid of binocular loupes and halogen lamp illumination. The Multifunctional Miniprobe® inner tube was connected to a source of androsta-4,16-dien-3β-ol in propylene glycol, for delivering the steroid aerosolized in a stream of clean air; the outer tube was connected to a source of negative pressure for scavenging the excess steroid delivered to the vomeronasal organ pit. The electrovomerogram recorded with the surface silverwire electrode was electronically amplified and continuously monitored in a computer and a dose-response curve was obtained by plotting the peak amplitude of electrovomerograms produced by several different amounts of androsta-4,16-dien-3β-ol (ranging from 0 (control) to 1000 picograms). Since there is a linear relationship between receptor occupancy and response (electrovomerogram amplitude), as in the model of A. J. Clark, the concentration of androsta-4,16-dien-3β-ol at which it is half maximally effective, the $EC_{50}$, is equal to its $K_D$. The $EC_{50}$ for androsta-4,16-dien-3β-ol is 0.5 nanograms ($K_{D\ androsta-4,16-dien-3\beta-ol}$=0.5 ng). Near maximal responses of the electrovomerogram to androsta-4,16-dien-3β-ol were obtained with 100 nanogram to 1000 nanograms directly delivered to the vomeronasal organ.

Androsta-4,16-dien-3β-ol tested in concentrations above the $EC_{50}$, directly delivered to the vomeronasal organ of 20 human female patients that had been clinically diagnosed with generalized anxiety disorder (GAD), significantly reduced acute anxiety symptoms scores (Hamilton Anxiety (HAM-A), Covi Anxiety (COVI) and Clinical Global Impression (CGI)) lasting 30 minutes after intranasal administration (Table 1).

TABLE 1

Mean acute symptom improvement in patients diagnosed with generalized anxiety disorder (n = 20) after delivery of 1 nanogram androsta-4,16-dien-3β-ol (ADOL) to the vomeronasal organ.

| TEST | TREATMENT | SYMPTOM IMPROVEMENT MEAN | S.D. | P = |
|---|---|---|---|---|
| HAM-A | PLACEBO | 5.0 | 5.5 | .036 |
|  | ADOL | 10.6 | 5.2 |  |
| COVI | PLACEBO | .8 | 1.3 | .019 |
|  | ADOL | 2.8 | 1.9 |  |
| CGI | PLACEBO | .62 | .52 | .046 |
|  | ADOL | 1.17 | .58 |  |

Mean Acute Symptom Improvement = (Mean Baseline Score − Mean Score after Treatment)
Statistical analysis: ANOVA. Significance level: 95% confidence intervals Androsta-4,16-dien-3β-ol formulated in water and delivered intranasally in spray form significantly reduced symptoms of acute anxiety disorder. Due to the hydrophobic properties of the steroid, dissolution in water was performed with the aid of co-solvents propylene glycol (0.5% to 5% w/v), ethanol (0.1% to 5% w/v) and Tween 80-R (0.01% to 2% w/v) and water (q.s. to 100%). Benzalkonium chloride (0.01% w/v) was used as a preservative. A commercially available, metered-dose, spray pump (Valois VP 7/50) was used for delivering a dose of androsta-4,16-dien-3β-ol y intranasally. After the spray pump was primed, each activation delivered a 50 μL spray of fine microdroplets (average diameter=700 μm). The effective quantity of androsta-4,16-dien-3β-ol delivered to the nasal mucosa in the area of the VNO was achieved by spraying intranasally with the spray nozzle directed toward the VNO opening and positioned at 1 centimeter from the anterior and lower nasal septum. Under these conditions the area of nasal septum that was sprayed was measured and the following extrapolations were done:

Average diameter of area sprayed (spray plume): 7 mm
Area sprayed=$r^2 \times \pi$=$(7\ mm)^2 \times 3.14$=154 $mm^2$
Average radius of the human VNO pit: 1.0 mm
Average area of the VNO pit: $r^2 \times \pi$=$(1)^2 \times 3.14$=3.14 $mm^2$
Ratio of nasal mucosa sprayed with spray pump VP 7/50 to VNO pit area:
Area sprayed/VNO pit area=154 $mm^2$/3.14 $mm^2$=51.3 (approx.=50)

Examples of the effective quantity of androsta-4,16-dien-3β-ol delivered to the vomeronasal organ pit with a 50 μL intranasal spray are shown in Table 2.

TABLE 2

Androsta-4,16-dien-3β-ol (MW = 272.43) reaching the vomeronasal organ pit during intranasal spray delivery with metered spray pump VP7/50

| Androsta-4,16-dien-3β-ol concentration in VP7/50 | Quantity (ng) of androsta 4,16-dien-3β-ol reaching nasal mucosa (area = 154 $mm^2$) | Effective quantity (ng) of androsta-4,16-dien-3β-ol reaching VNO pit |
|---|---|---|
| 5 × 10$^{-3}$ | 68107.5 | 1362.15 |
| 10$^{-3}$ | 13621.5 | 272.4 |
| 10$^{-4}$ | 1362.15 | 27 |
| 10$^{-5}$ | 136.215 | 2.7 |
| 4 × 10$^{-5}$ | 54.5 | 1 |

The effective quantity of androsta-4,16-dien-3β-ol delivered to the patient's vomeronasal organ pit was 1 nanogram, which is approximately twice the $EC_{50}$. This quantity significantly improved symptoms of social anxiety (see Table 1).

The pharmaceutical formulation of androsta-4,16-dien-3β-ol may optionally further include an excipient added to the composition in an amount sufficient to enhance the stability and the volatility of the composition, and/or to maintain the product in solution. Examples of excipients include but are not limited to propylene glycol, ethanol, Tween 80-R, hydroxipropyl-β-cyclodextrin and biopolymers. For example, the composition may be incorporated into a solution with propylene glycol, suitable for intranasal administration in vapor form.

The composition may be diluted into an aqueous solution using de-ionized water to form a pharmaceutical formulation with adjusted to pH 7.4 adding phosphate buffer for intranasal delivery as a liquid spray. Such pharmaceutical formulation consists of ADOL, 1% to 5% propylene glycol, 0.05 to 1% Tween 80-R, phosphate buffer and de-ionized water (as needed).

The pharmaceutical formulations used herein contain one or more pharmaceutically acceptable carriers (also termed excipients or vehicles) suited for the particular type of formulation, i.e. vapor, liquid, gel, ointment or the like. The vehicles are comprised of naturally occurring or synthetic compounds or materials that do not adversely affect androsta-4,16-dien-3β-ol or other components of the formulation. Suitable carriers for use herein include water, silicone, waxes, petroleum jelly, propylene glycol, liposomes, and a variety of other materials.

The pharmaceutical formulations of the invention are typically contained within drug delivery systems which provide a specific, predetermined agent release profile, i.e.: single dose or multidose metered delivery device. Such systems can include for example metered spray pumps, aerosols and nasal inhalers Drug delivery platforms comprise aerosols capable of providing powder delivery of androsta-4,16-dien-3β-ol using air as propellant. The powder consists of particles of 10 m to 500 μm diameter and of native androsta-4,16-dien-3β-ol crystals mixed with casein, dextrose or lactose as an excipient, to achieve adequate concentration and particle size for intranasal delivery.

A device for the treatment of social phobia may be a drug delivery device adapted to deliver an effective amount of an androsta-4,16-dien-3-ol steroid to a patient. The androsta-4,16-dien-3-ol steroid to be delivered may be androsta-4,16-dien-3β-ol, androsta-4,16-dien-3α-ol, or both androsta-4,16-dien-3β-ol and androsta-4,16-dien-3α-ol. The androsta-4,16-dien-3-ol steroid may be delivered in a liquid, vapor, or ointment, or any other suitable form. Such a drug delivery device may include an elongated portion, such as tube or nozzle, for delivering the androsta-4,16-dien-3-ol steroid to the vomeronasal organ of a patient. The elongated portion may be a thin tubular portion, an may be a thin tubular flexible portion, suitable for insertion into a nasal passage of a patient.

Other drug delivery platforms capable of providing a pulsatile release profile include topic vapor delivery from a mineral oil or propylene glycol based swab or ointment applied to the skin of the face near the nose or the upper lip. This delivery method would use the movement of air during respiration as carrier of androsta-4,16-dien-3β-ol vapors delivered from the ointment or the swab to the nasal passages. Such delivery provides for sustained or chronic delivery of the drug.

Transmucosal delivery may be had from an intranasal water-based solution delivered in spray form to the nasal passages. The water based solution could, for example, contain the excipients as described above.

Other excipients that may be added to the formulation of androsta-4,16-dien-3β-ol include odorants, such as, for example, primary odors such as vanillin or floral odors. Vanillin and floral odors could be used to "prime" or to "condition" the patient so as to enhance the effect of the medication delivered intranasally. Since androsta-4,16-dien-3β-ol is odorless, adding an odor to the formulation would indicate to the patient the efficacy of medication delivery to the nasal passages. Also, an absence of odor would indicate a failure to deliver the compound to the nasal passages, or that the delivery device was empty.

Suitable devices for nasal delivery of androsta-4,16-dien-3β-ol include:

A) metered spray pump; delivers a volume between 15 and 100 μl, and no less than 10 and no more than 500 μl of water based spray containing the effective dose of androsta-4,16-dien-3β-ol to the nasal passages. With the tip of the applicator (nozzle) positioned between about 5 mm and about 20 mm of the nasal septal mucosa, particularly about 10 mm to about 15 mm, the average area of nasal mucosa sprayed is about 154 $mm^2$. The ratio of area of nasal mucosa sprayed to vomeronasal organ area is about 50:1. The effective nasal dose of androsta-4,16-dien-3β-ol is represented in Table 2.

B) A powder nasal applicator; delivers the effective dose of androsta-4,16-dien-3β-ol, formulated with another excipient in powder form (e.g., casein, dextrose or sucrose) to the nasal passages. The particle size of the powder is typically between about 10 and about 500 μm, particularly between about 100 and about 300 μm. The effective dose for androsta-4,16-dien-3β-ol is represented in Table 2.

C) Vapor nasal delivery device having androsta-4,16-dien-3β-ol in propylene glycol, impregnated in a cotton (USP) pellet. Vapors from the device deliver the effective dose of androsta-4,16-dien-3β-ol to the nasal passages during breathing, inhalation or sniffing. D) Swab containing androsta-4,16-dien-3β-ol in mineral oil based ointment, or in solution with propylene glycol for local, topic application to the surface skin of the upper lip or the face. Respiration (inspiration) carries the effective dose of the substance in vapor form to the nasal passages during a period of 4 to 6 hours.

EXAMPLES

The following Example is intended to illustrate but not to limit the invention.

A Phase-2 Randomized, Double-blind, Crossover Study of the Use of Single Doses of [3β]-Androsta-4,16-dien-3-ol for Management of the Symptoms of Social phobia The following describes a study of the effects of the vomeropherin [3β]-androsta-4,16-dien-3-ol on human female patients suffering from social phobia.

The study comprised 40 patients with clinical diagnosis of Social Phobia. Each patient was randomly assigned to one of the following double-blind treatment groups: 800 nanogram [3β]-Androsta-4,16-dien-3-ol or placebo delivered intranasally in spray form. Each patient participated in the Treatment Phase as follows.

First Visit: the patient visited the study center and the following activities were conducted during this visit: Pre-Challenge: After arrival at the study center, the patient completed self-reports of her usual anxiety symptoms. Public Speaking Challenge: The patient was administered a spray (50 microliters) of placebo to each nostril, and the procedures for the Public Speaking Challenge were then explained to the patient. The patient was given four minutes to prepare one of several topics for a four-minute speech, without notes, in front of an audience of several people who evaluated the speech and videotaped it. Immediately after completing the preparation period, the patient completed self-reports of her anticipatory anxiety and the Investigator then rated the patient's anticipatory anxiety. The patient gave her speech. Immediately after completing the speech, the patient completed self-reports of anxiety experienced during the speech. The Investigator then rated the anxiety experienced by the patient. Social Interaction Challenge: Approximately one hour after completion of the Public Speaking Challenge, the patient was administered another dose of placebo in each nostril, and the procedures for a Social Interaction Challenge appropriate for one of the patient's most-feared social interaction situations were then described to the patient. Then, the patient completed self-reports of her anticipatory anxiety and the Investigator rated the patient's anticipatory anxiety. Then, the patient participated in a four-minute mock social interaction while being observed by several raters and videotaped. Immediately after completing the social interaction, the patient completed self-reports of anxiety experienced during the interaction. Then, the Investigator rated the anxiety experienced by the patient. Those patients that during the first visit responded to placebo during the public speaking or the social interaction challenge were terminated from the study at that time. Patients non-responding to placebo during the first visit participated in a second visit where they were randomly dosed again with placebo, or with 800 nanograms androsta-4,16-dien-3β-ol per nostril (total dose=1,600 nanograms) delivered in spray form. Each patient was challenged and also the anxiety symptoms were scores using the same procedure performed during first visit.

Results: The mean score obtained during the first visit (baseline scores) for each, anticipatory public speaking, performance public speaking, anticipatory social interaction and performance social interaction, was substracted from the mean score (same parameter) obtained during the second visit. The result is a measure of symptom improvement. As shown in Table 3, androsta-4,16-dien-3β-ol induced much greater and significant symptom improvement than placebo.

A statistically significant difference between groups and within patients, between androsta-4,16-dien-3β-ol treatment and placebo treatment was demonstrated for Anticipatory and Performance Anxiety during Social Interaction and Public Speaking. Anticipatory and Performance anxiety scores were notably and significantly decreased (improvement) 5 minutes after administration of androsta-4,16-dien-3β-ol. Therefore, efficacy of androsta-4,16-dien-3β-ol for the treatment of moderate to severe symptoms of acute anxiety was demonstrated.

TABLE 3

Acute treatment of patients diagnosed with generalized social phobia (n = 40) with 1600 nanogram androsta-4,16-dien-3β-ol (ADOL) delivered intranasally improves symptoms significantly different from placebo.

| Anxiety | Treatment | Mean Symptom Improvement | S.D.M. | P = |
|---|---|---|---|---|
| Anticipatory Social Interaction Anxiety | Placebo | 6.251 | 13.377 | .04 |
| | ADOL | 12.166 | 12.660 | |
| Performance Social Interaction Anxiety | Placebo | 2.185 | 26.485 | .02 |
| | ADOL | 14.197 | 12.208 | |
| Anticipatory Public Speaking Anxiety | Placebo | −5.593 | 26.510 | .03 |
| | ADOL | 10.417 | 14.738 | |
| Performance Public Speaking Anxiety | Placebo | 17.123 | 22.870 | .02 |
| | ADOL | 26.294 | 27.423 | |

Symptom Improvement: Mean Baseline Score − Mean Score After Treatment.
Statistical Analysis: ANOVA. Significance level: 95% confidence intervals.

What is claimed is:

1. A method to reduce the acute social phobic response in an individual suffering from social phobia and about to experience or already experiencing a social or performance situation, the method comprising administering to the vomeronasal organ of the individual, while the individual is about to experience or already experiencing the social or performance situation, an amount of androsta-4,16-dien-3β-ol effective to reduce the social phobic response for less than about five hours.

2. The method of claim 1 where the individual is a woman.

3. The method of claim 1 where the social phobia is generalized social phobia.

4. The method of claim 1 where the social phobia is specific social phobia.

5. The method of claim 1 where the individual is about to experience a social situation.

6. The method of claim 1 where the individual is about to experience a performance situation.

7. The method of claim 1 where the individual is already experiencing a social situation.

8. The method of claim 1 where the individual is already experiencing a performance situation.

9. The method of claim 1 where the reduction in social phobic response is for less than about three hours.

10. The method of claim 9 where the reduction in social phobic response is for less than about one hour.

11. The method of claim 1 where the effective amount is between about 100 pg and about 100 µg.

12. The method of claim 11 where the effective amount is between about 1 ng and about 100 µg.

13. The method of claim 12 where the effective amount is between about 10 ng and about 1 µg.

14. The method of claim 1 where the androsta-4,16-dien-3β-ol is administered in a pharmaceutical composition.

15. The method of claim 14 where the pharmaceutical composition is a liquid, an ointment, or a powder.

16. The method of claim 15 where the pharmaceutical composition is a liquid.

17. The method of claim 16 where the pharmaceutical composition is an aqueous solution.

18. A method to reduce the acute social phobic response in a woman suffering from social phobia and about to experience a social or performance situation, the method comprising administering to the vomeronasal organ of the woman, while the woman is about to experience the social or performance situation, androsta-4,16-dien-3β-ol in an amount effective to reduce the social phobic response for less than about five hours, the administering comprising spraying into each nostril an aqueous solution of androsta-4,16-dien-3β-ol containing 800 ng androsta-4,16-dien-3β-ol per administration.

19. The method of claim 18 where the volume of the aqueous solution administered is 50 µL per administration.

20. The method of claim 18 where the woman is about to experience a social situation.

21. The method of claim 18 where the woman is about to experience a performance situation.

22. The method of claim 20 where the performance situation is giving a speech.

* * * * *